United States Patent [19]

Evensen et al.

[11] 4,097,644

[45] Jun. 27, 1978

[54] INORGANIC RAW FELT INTENDED FOR THE PRODUCTION OF ROOF FELT

[75] Inventors: Harald Thiis Evensen, Porsgrunn; Ola Tellesbo, Heistad, both of Norway

[73] Assignee: Isola Fabrikker A/S, Brevik, Norway

[21] Appl. No.: 602,001

[22] Filed: Aug. 5, 1975

Related U.S. Application Data

[63] Continuation of Ser. No. 256,427, May 25, 1972, abandoned.

[30] Foreign Application Priority Data

May 26, 1971 Norway .................................. 711988

[51] Int. Cl.$^2$ .......................... D04H 1/08; C08K 7/14
[52] U.S. Cl. .................................... 428/281; 162/145; 162/155; 162/165; 162/169; 260/2.3; 260/4 R; 260/28.5 AS; 260/33.6 R; 260/42.18; 264/112; 264/113; 427/186; 427/195
[58] Field of Search ............... 260/2, 3, 4 R, 28.5 AS, 260/33.6, 42.18; 428/281, 283, 372, 323, 327; 427/186, 195; 264/112, 113; 162/145, 169, 168 R

[56] References Cited

U.S. PATENT DOCUMENTS

| | | | |
|---|---|---|---|
| 2,555,401 | 6/1951 | Fasold et al. ........................ 427/186 |
| 2,717,841 | 9/1955 | Biefeld et al. ..................... 428/372 X |
| 2,746,894 | 5/1956 | Orser et al. ....................... 264/112 X |
| 3,030,223 | 4/1962 | Alstad et al. ..................... 428/327 X |
| 3,087,830 | 4/1963 | Schuller ............................... 427/186 |
| 3,137,100 | 6/1964 | Harshberger ........................ 50/198 |
| 3,144,379 | 8/1964 | Gelbert ............................ 162/169 X |
| 3,155,567 | 11/1964 | Harr ..................................... 428/372 |
| 3,184,373 | 5/1965 | Arledter ....................... 162/168 R X |
| 3,193,446 | 7/1965 | Eisenberg ............................ 162/145 |
| 3,223,580 | 12/1965 | Eckert et al. ........................ 162/145 |
| 3,228,790 | 1/1966 | Sexsmith et al. ................ 428/327 X |
| 3,310,459 | 3/1967 | Guthrie ............................ 162/169 X |
| 3,489,710 | 11/1970 | Bonotto et al. .................... 260/33.6 |
| 3,622,447 | 11/1971 | Oosterbeek et al. ............ 162/169 X |
| 3,630,833 | 12/1971 | Fife ..................................... 162/163 |
| 3,729,373 | 4/1973 | Hildbrand et al. .............. 162/145 X |
| 3,745,060 | 7/1973 | Jumentier et al. .................. 428/372 |
| 3,909,346 | 9/1975 | Winters ........................... 162/169 X |
| 3,914,498 | 10/1975 | Videen ............................ 264/112 X |

FOREIGN PATENT DOCUMENTS

| | | |
|---|---|---|
| 694,242 | 9/1964 | Canada. |
| 522,694 | 3/1956 | Canada. |
| 688,690 | 6/1964 | Canada. |
| 696,408 | 10/1964 | Canada. |

*Primary Examiner*—Thomas DeBenedictis
*Attorney, Agent, or Firm*—Watson, Cole, Grindle & Watson

[57] ABSTRACT

An improved raw felt material having a high degree of strength and flexibility and increased bulk. The raw felt is used in producing an asphalt roofing cover. The felt is formed from an adhesively bonded porous nonwoven sheet of an inorganic fibrous material and has finally divided vulcanized rubber particles distributed within the fibrous material.

8 Claims, No Drawings

INORGANIC RAW FELT INTENDED FOR THE PRODUCTION OF ROOF FELT

This is a continuation of application Ser. No. 256,427 filed May 25, 1972 and now abandoned.

The present invention relates to a raw felt for roof felt, consisting of inorganic fibers and binding material and characterized in the addition of 0.5 - 50% by weight as calculated on the total weight of finely divided, vulcanized rubber or another high polymer material having equivalent qualities.

Roof felt based on wool felt or cellulose felt tends to a certain degree to absorb moisture or to give out moisture under varying climatic conditions. The variable moisture content will cause the felt to expand and contract, and this also may cause the formation of blisters due to steam occlusions. Also, such organic fibers tend to decay.

It is thus desirable to use a raw felt of inorganic fibers. Such felts have previously been developed based on e.g. various qualities of glasfiber. Most available qualities have a weight of 50–70g/m$^2$ and such products (also called glass vliess) have found extensive use as on underlaying felt; however, these thin glass vliess materials have often been used as overlaying felt. An important objection to the use of glass vliess often as an overlaying felt is that the raw felt has a thickness of only about 0.4 mm, whereas a top layer wool felt has a thickness of about 1.4 mm. If there should be oxidation crevices or other faults in the coating, leakages might easily occur in these thin glass fiber felts, whereas the wool felt still has an impregnated felt thickness of about 1.4 mm. The thickness of the raw felt also is directly related to its fire protection qualities.

If one tries to produce a thicker glass vliess (more than 70 g/m$^2$ from continually drawn glass fibers which are cut from a higher quality glass staple fiber, the price of the product would easily become too high. To keep costs on an acceptable level one may admix cheap inorganic fibers (like glass wool, rock wool, lower asbestos fiber qualities and the like). These cheap fibers are comparatively weak and brittle, and a thick glass vliess with such fibers added would be stiff and brittle. More flexibility may be achieved by use of special flexible glue, but then the product will have a considerably lower breaking strength.

SUMMARY OF THE INVENTION

The object of the present invention is thus to provide an inorganic raw felt having a commercially desirable thickness and a reasonable price coupled with commercially acceptable flexibility and strength characteristics. This is achieved according to the present invention by forming a thick glass felt from a mixture of inorganic fibers, a binding agent and 0.5–50% by weight of finely divided, vulcanized rubber particles. The rubber powder may be produced by pulverizing tire threads, and a rubber powder finer than 40 mesh may be used. Such rubber powders are utilized as an additive for asphalt mixtures with the object of providing better thermal qualities. Pulverized motor car tire thread generally consist of a mixture of the rubbers including both natural rubber and synthetic rubber and the expression "rubber" used herein thus encompasses both of these kinds of rubber as well as other high polymeric materials having equivalent qualities. The mixture of inorganic fibers and rubber powder is cemented in the production process in the usual manner by aid of a suitable glue. Among the conventional glues which may be used for such purposes are urea formaldehyde, polyacrylic acid ester, polyvinyl alcohol having a high degree of hydrolyzation and other known glues and mixtures of same. The vliess may also be produced in various manners. Generally, the vliess is formed utilizing either aerodynamic dry processes or wet processes in a hydroformer. After the vliess has been formed, a water dispersion solution of the glue is applied to the vliess by dipping or by spraying. The glue is then dried and hardened if desired. The glue may also be applied to the fibers before the vliess is formed, either by a so called "beater deposition" method or by mixing the glue solution and the fibers before the vliess is formed in the hydroformer.

The rubber particles admixed in the vliess form flexible "bridges" or "buffers" providing the glass felt with a greater flexibility without reducing its breaking strength in spite of a high weight and a large content of brittle fibers. Such felts generally have a thickness of about 1 mm or more whereby oxidation ruptures and the like will not cause any great danger of leakages. Such felts may thus be used as top layer felts.

Another advantage achieved is that the rubber powder contributes to the increasing of the bulkiness and therefor the porosity of the glass felt. The rubber powder also facilitates fixing of the asphalt in the felt.

EXAMPLE

One square meter of a raw felt having a weight of 150 g/m$^2$ is produced from the following composition:

50 grams of textile glass fibers cut into lengths of 6 mm (chopped strand), 50 grams of glass wool (insulation wool), 32 grams of rubber powder finer than 40 mesh produced by pulverization of motor car tire treads and 18 grams of a polyvinyl alcohol glue having a high degree of hydrolyzation. The thickness of the felt is about 1 mm. The product has a commercially acceptable strength and flexibility as well as a favorable price. The textile glass fibers together with the glue provide a sufficient strength while the glass wool fibers and the rubber particles provide thickness and reinforcement for the asphalt. The rubber powder is necessary to the provision of the desired strength and reinforcement to the asphalt and to the provision of flexibility to the finished product. The felt product of the present invention is produced by the following procedure: first the fibrous materials and the rubber powder are suspended in a 5% solution of the polyvinyl alcohol; secondly the suspension of fibrous materials and rubber powder is processed on an inclined wire hydroformer whereby a wet felt product is formed; thereafter excess polyvinyl alcohol solution is filtered off; and finally the felt is dried and the glue in the felt is hardened.

We claim:

1. A raw felt possessing improved strength, flexibility and bulk, for use in producing an asphalted roofing covering, said raw felt comprising an adhesively bonded porous non-woven sheet of an inorganic fibrous material selected from the group consisting of glass fibers, asbestos fibers and mixtures thereof, and 0.5 – 50% by weight, based on the total weight of the raw felt, of finely divided vulcanized rubber particles distributed with said fibrous material.

2. Raw felt as defined in claim 1, wherein said finely divided vulcanized rubber particles have a particle size finer than 40 mesh.

3. Raw felt as defined in claim 2, wherein said finely divided vulcanized rubber particles are particulated members formed from a rubber tire.

4. Raw felt as defined in claim 2, wherein said finely divided vulcanized rubber particles comprise a mixture of particulated natural and synthetic rubbers.

5. Raw felt as defined in claim 2, wherein said adhesive for binding said fibrous material is selected from the group consisting of urea formaldehyde, as ester of polyacrylic acid, polyvinyl alcohol having a high degree of hydrolyzation and mixtures thereof.

6. Raw felt as defined in claim 2, wherein said inorganic fibrous material comprises glass fibers.

7. Raw felt as defined in claim 7, wherein said inorganic fibrous materials comprises glass fibers admixed with another inorganic fibrous material.

8. Raw felt as defined in claim 7, wherein said another inorganic fibrous material is glass wool.

* * * * *